United States Patent [19]
Levine

[11] 4,259,964
[45] Apr. 7, 1981

[54] DEVICE FOR OBTAINING STOOL SAMPLES

[76] Inventor: Robert A. Levine, 31 Pilgrim La., Guilford, Conn. 06437

[21] Appl. No.: 55,636

[22] Filed: Jul. 9, 1979

[51] Int. Cl.³ .............................................. A61B 10/00
[52] U.S. Cl. .................................. 128/638; 128/759; 128/283; 422/61; 23/931
[58] Field of Search ............... 128/638, 749, 759, 760, 128/771, 283; 422/50, 56, 58, 60, 61; 23/DIG. 931

[56] References Cited

U.S. PATENT DOCUMENTS

| | | | |
|---|---|---|---|
| 2,292,450 | 8/1942 | Kohn | 128/760 X |
| 2,969,057 | 1/1961 | Simmons | 128/759 |
| 3,282,114 | 11/1966 | Pell | 128/759 |
| 3,666,421 | 5/1972 | Price | 422/58 X |
| 3,785,930 | 1/1974 | Ellis | 422/56 |
| 3,965,888 | 6/1976 | Bender | 128/759 |
| 3,996,006 | 12/1976 | Pagano | 422/50 |
| 4,092,120 | 5/1978 | Suovaniemi et al. | 422/58 X |
| 4,108,729 | 8/1978 | Mennen | 422/56 X |
| 4,199,550 | 4/1980 | Wielinger et al. | 422/58 |

FOREIGN PATENT DOCUMENTS

| | | | |
|---|---|---|---|
| 655678 | 1/1963 | Canada | 128/760 |
| 1212404 | 10/1959 | France | 128/759 |
| 7805023 | 11/1978 | Netherlands | 128/749 |

*Primary Examiner*—Kyle L. Howell
*Attorney, Agent, or Firm*—William W. Jones

[57] ABSTRACT

The device is usable by a patient to self-obtain a stool sample for use in testing for gastro-intestinal bleeding. The device is a multi-layered pad which can be dispensed by a physician or the like to the patient and which the patient can use in privacy. The device is used in the same manner as toilet tissue to obtain the stool sample after defecation. Excess stool sample is discarded in the toilet and an appropriate amount of the stool sample is retained on the pad. The pad is then sealed and returned to the physician or testing laboratory hermetically sealed. The seal is broken, the test is performed, and then the pad is resealed hermetically and discarded.

10 Claims, 5 Drawing Figures

DEVICE FOR OBTAINING STOOL SAMPLES

This invention relates to a stool sampling device which can be used by a patient, in the same manner as toilet tissue, to obtain a stool sample which can then be tested for signs of gastro-intestinal bleeding.

One medical procedure frequently used on physicians' patients involves the obtaining of a stool sample which is tested for traces of blood to determine the presence or absence of gastro-intestinal bleeding. This test is a conventional precaution for patients having an established history of gastro-intestinal bleeding and will also be used on patients who are anemic, and who complain of gastro-intestinal discomfort. This test is also used as a screening test during routine physical examinations.

A manner most commonly used to obtain the stool sample is by the physician's donning a rubber glove and manually inserting a finger into the rectum of the patient to obtain a stool smear. The stool is then transferred to a piece of absorbent paper and effective amounts of detecting agents such as guaiac, ortho-tolidine, or ortho-dianisidine and hydrogen peroxide are applied to the stool whereupon the presence of blood in the stool will cause a bluish coloration to appear. No color change indicates the absence of occult blood in the stool, and therefore, the absence of gastro-intestinal bleeding. This method of obtaining the stool sample is not sanitary and unpleasant for the patient and for the physician.

Another method for obtaining the required stool samples involves the use of a kit sold under the brand name Hemoccult by Smith Kline Diagnostics. The kit includes a packet made of paper and formed somewhat similarly to a match book. The packet has a tab-slot interlock which can be opened so that the packet can be unfolded. Inside of the packet there is disposed a sample-receiving pad which has been treated with guaiac, one of the detecting chemicals referred to above. A sample-obtaining wooden stick is included with the kit. The kit is designed for use by the patient in privacy as follows. The kit is given to the patient by the physician, or obtained at a pharmacy upon directive of the physician. The patient takes the kit home, and it is used subsequent to defecation. A scraping of the bowel movement is obtained by the patient from the toilet with the stick and some of the scraped material is transferred to the pad from the stick. The contaminated stick must then be discarded by the patient. The packet flap is then reclosed and the packet and sample are then returned to the physician's office for examination. It will be appreciated that this procedure is to some extent more desirable than the first above-described procedure in that it may be performed in privacy. Nevertheless, it is also an unclean procedure with no provision for guarding against contamination, and the manner of disposition of the specimen on the pad is somewhat distasteful in that the stool-contaminated pad is generally discarded in the trash in an unsealed state.

Other prior art stool sampling devices are disclosed in U.S. Pat. Nos. 3,718,431; 3,672,351; and 3,996,006.

I have devised a device which is used to procure stool samples, and which may be used in a conventional manner, in the privacy of one's home, or toilet in a physician's clinic or office, and which is clean and contamination-free. Briefly, the device of my invention is a pad or packet having a number of constituent layers, the pad being used to obtain the stool specimen in the same manner as toilet tissue after defecation. Excess amounts of stool are removed from the pad by tearing off one of the constituent layers and discarding that layer in the toilet, that layer being biodegradable. The pad is then hermetically sealed and returned to the physician's office. The device is thus contamination and odor-free during transport. To examine the specimen for blood, the pad is opened and the reagent applied to the stool sample. Inspection for color change is made, and the pad is resealed and discarded. In this manner, the test is performed quickly, and the discarded pad is both contamination and odor-free.

It is, therefore an object of this invention to provide a device for the taking of stool samples to be used in performing blood-detecting testing.

It is an additional object of this invention to provide a device of the character described which can be used by a patient in the privacy of his home and at his convenience.

It is yet another object of this invention to provide a device of the character described which is used in a conventional manner, and which is contamination and odor-free.

These and other objects and advantages of this invention will be more readily understood from the following detailed description of a preferred embodiment thereof taken in conjunction with the accompanying drawings, in which.

Figure 1:
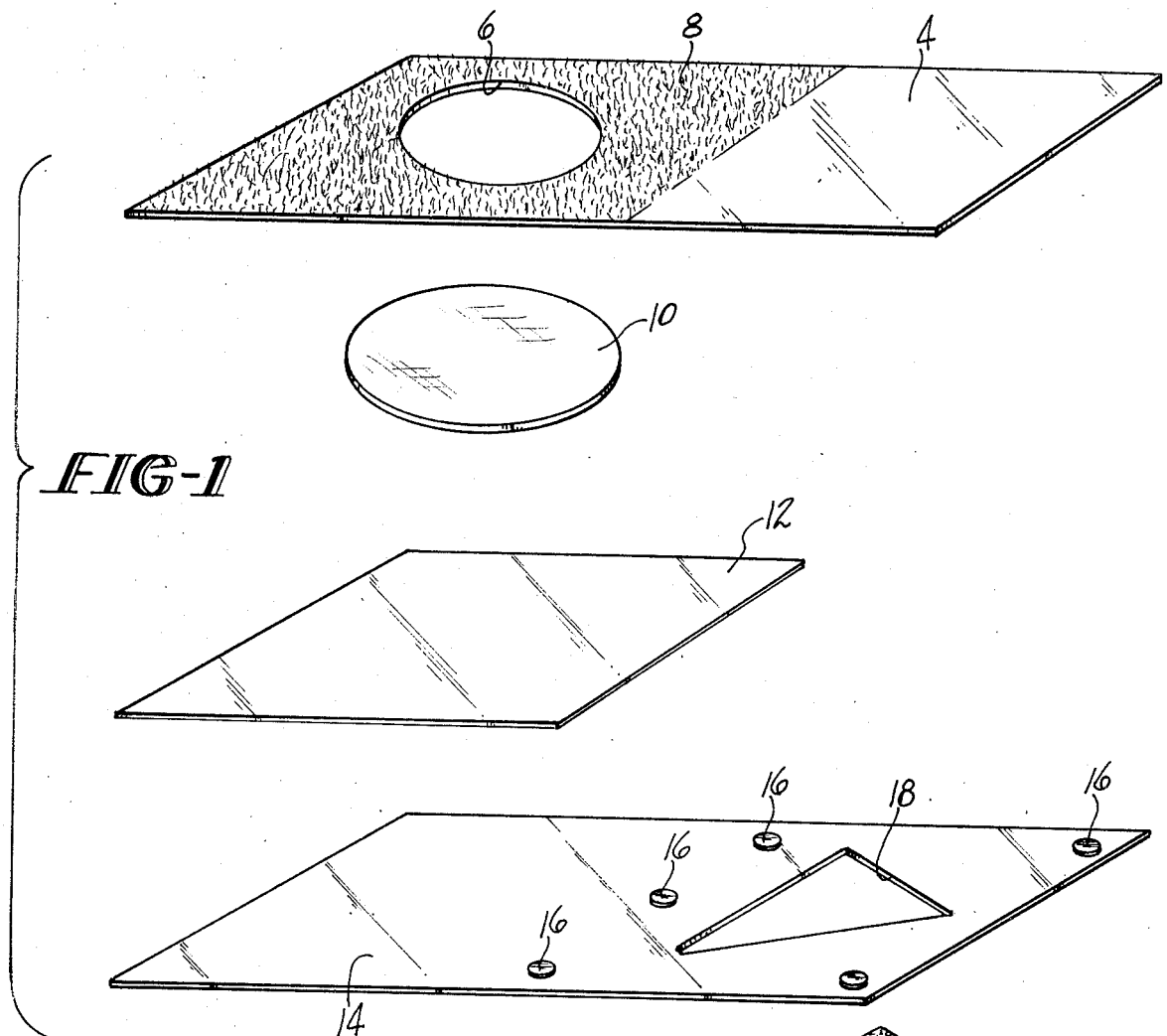
FIG. 1 is an exploded perspective view of a preferred embodiment of a device made in accordance with this invention.

Referring now to the drawings, there is illustrated a preferred embodiment of the stool sampling device of my invention. The device, denoted generally by the numeral 2, is a multi-layered assemblage which has the general pliancy and feel of a thickened piece of toilet tissue. The upper layer 4 is a sheet of semi-flexible material such as polyethylene plastic; paper-plastic laminate, or the like. On one side of the upper sheet 4, there is disposed an opening 6. The half of the sheet 4 which contains the opening 6 has deposited thereon a layer 8 of soft fibrous cellulosic material which is flocked onto the sheet 4 and provides the flocked half thereof with a soft texture similar to tissue paper. Thus, one half of the sheet 4 will have a soft, tissue-like texture, and the other half will have a smooth, shiny texture, like plastic.

Disposed beneath the opening 6, there is a somewhat enlarged pad 10 of absorbent paper, or the like. An adhesive layer 12 underlies the pad 10 and serves to secure the pad 10 and the flocked half of the overlying sheet 4 to a bottom sheet 14, which is formed from an impermeable material such as a paper-plastic laminate, a foil-plastic laminate, or the like. The bottom sheet 14 is also semi-flexible so as to maintain the overall flexibility and pliability of the entire laminate. The layer 12 may take the form of a double-sided sticky tape, or may be simply a layer of sticky, resealable adhesive coated directly on the sheet 14. Disposed on the half of the bottom sheet 14 not covered by the adhesive layer are a plurality of adhesive buttons 16 which serve to releasably adhere the nonflocked half of the sheet 4 to the sheet 14. The sheet 14 is provided with an opening 18 on one of its halves, and the opening 18 is closed and sealed by means of a conforming closure member 20 made from the same material as the sheet 14. The closure member 20 includes a pull tab 22 and a border 24 of resealable adhesive which serves to secure the closure member 20 to the sheet 14.

Figure 2:
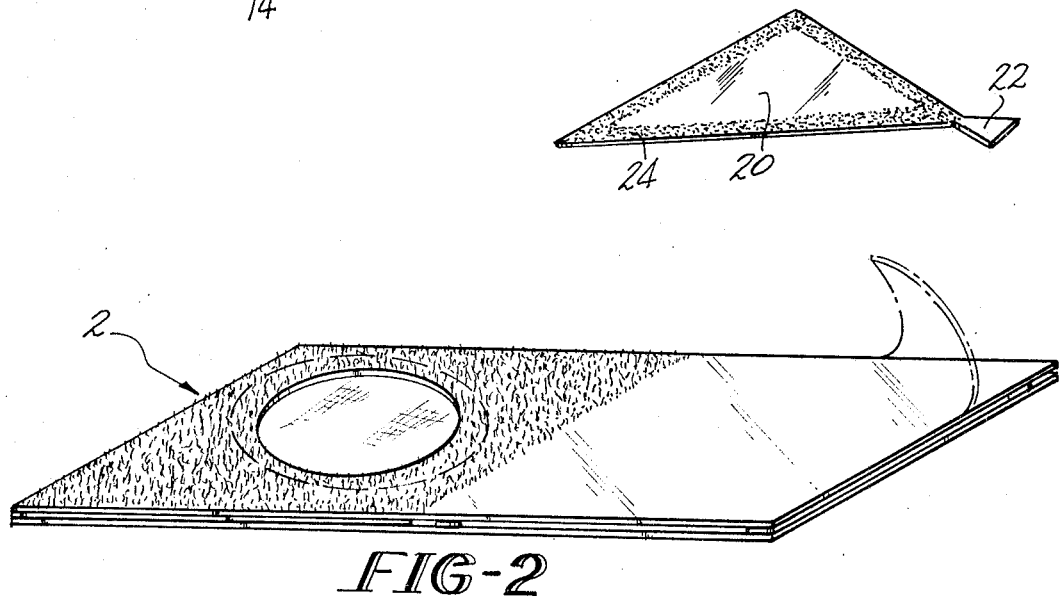
FIG. 2 is a perspective view of the device of FIG. 1.

The appearance of the device 2 as dispensed by the physician, pharmacy, or the like, in its ready-to-use condition, is shown in FIG. 2.

The device 2 is used to obtain a stool sample in the following manner. Immediately after defecation, the device is used in the same manner as one uses toilet tissue, and the flocked portion of the device is drawn across the anus, whereby a stool smear is obtained on the flocking 8 and on the portion of the pad 10 which underlies the opening 6. The sheet 4 is then pulled away from the remaining portions of the device and discarded into the toilet where it is flushed away with the stool. It will be noted that the adhesive buttons 16 will easily allow the corresponding half of the sheet 4 to be removed from the sheet 14 (as shown partially in phantom in FIG. 2) whereupon the remainder of the sheet 4 and the flocked portion 8 thereon will be peeled off of the resealable adhesive layer 12.

Figure 3:
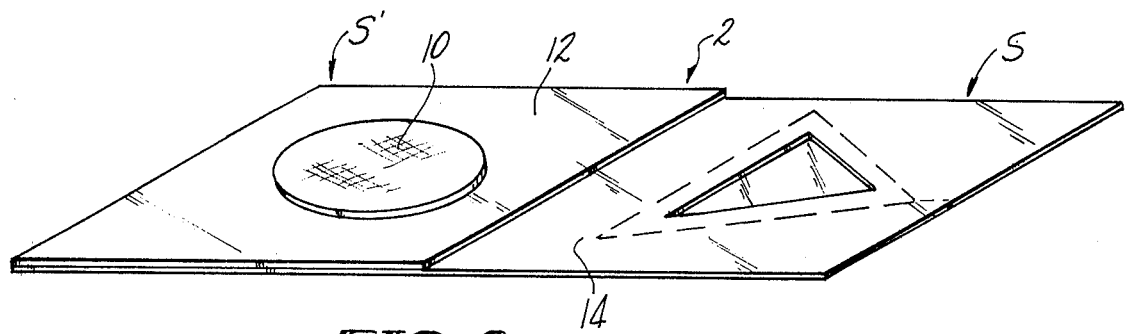
FIG. 3 is a perspective view of the device shown after the layer containing excess stool has been removed and discarded.
Figure 4:
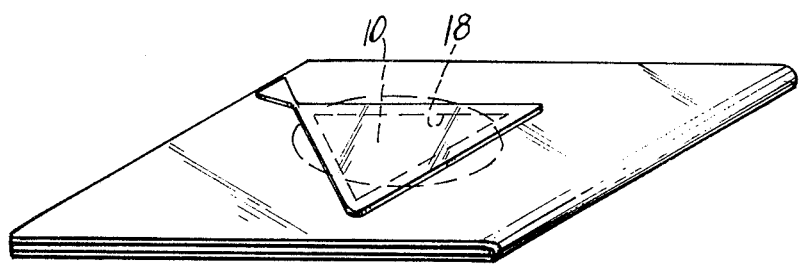
FIG. 4 is a perspective view of the device shown after the hermetic seal has been achieved to render the device contamination and odor-free.

After the sheet 4 has been removed from the device 2, the latter appears as shown in FIG. 3. It will be noted that the pad 10, upon which stool has been deposited, remains adhered to the adhesive layer 12. The half S of the sheet 14 is then folded over on top of other half S' of the sheet 14 to form a pouch configured as shown in FIG. 4. The folded-over half S is pressed against the exposed surface of the adhesive layer 12 so as to hermetically seal the resulting pouch whereby contamination and odor from the encased stool sample is prevented. It will be noted that the folding operation brings the sealed openings 18 into overlying relationship with the pad 10.

Figure 5:
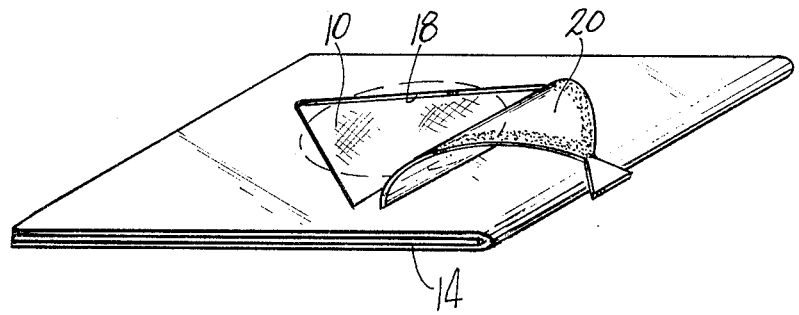
FIG. 5 is a perspective view of the device showing how access to the stool sample is made for performing the test.

The sealed pouch is then delivered to the physician's office, testing laboratory, or the like, wherein the encased stool sample will be tested for occult blood. To expose the stool sample for testing, the closure member 20 is peeled back from the opening 18, as shown in FIG. 5. The appropriate reagents are then applied to the stool sample on the pad 10. After the test has been performed, the closure member 20 is resealed over the opening 18 and the used pouch is discarded, in an hermetically sealed condition, for subsequent disposal, as by incineration or the like. It will be noted that, during the testing procedure, the underlying portion of the sheet 14 provides an impermeable barrier which prevents reagents, fecal material, viruses, bacteria, or the like from seeping through the pouch onto the laboratory bench, etc.

It will be readily appreciated that the device of this invention provides a means for obtaining a stool sample which is simple and natural to use, which can be used by a patient in privacy, and which circumvents the embarrassing aspects of the prior art devices and procedures. The sample, once obtained, is hermetically sealed whereby contamination and odor problems are avoided. Still further, the device enables the actual test to be performed without the possibility of reagent or contamination leakage occurring, and also enables the discarded tested stool sample to be contained in an hermetically sealed pouch.

Since many changes and variations of the disclosed embodiments of the invention may be made without departing from the inventive concept, it is not intended to limit the invention otherwise than as required by the appended claims.

What is claimed is:

1. A biological material sampling device for receiving and transporting material samples, said device comprising: a sheet of pliant impermeable material; absorbent means on said sheet for receiving a biological material smear; securement means disposed on said sheet and positioned to surround said absorbent means when said sheet is folded whereby said sheet can be folded onto said securement means to form a sealed impermeable pouch containing said absorbent means after reception of a biological material smear on said absorbent means; and means for opening said pouch for exposing said absorbent means for analysis of said biological material smear.

2. The device of claim 1 wherein said means for opening said pouch is resealable whereby said pouch can be resealed after a biological material analysis is made.

3. A stool sampling device for obtaining direct anal stool samples, said device comprising: a pliant sheet-like member; absorbent means secured to said sheet-like member for receiving a stool smear when said absorbent means is drawn across a patient's anus after defecation; adhesive means disposed on said sheet-like member to surround said absorbent means when said sheet-like member is folded whereby said sheet-like member can be folded onto said adhesive means to form a sealed pouch containing said absorbent means; and means for opening said pouch for exposing said absorbent means for application of chemical reagents thereto.

4. A stool sampling device for obtaining direct anal stool samples, said device comprising: a pliant sheet of impermeable material; absorbent means secured to said sheet for receiving a stool smear when said absorbent means is drawn across a patient's anus after defecation; adhesive means disposed on said sheet surrounding said absorbent means; impermeable closure means adapted to overlie said absorbent means and to be secured by said adhesive means to said sheet to form a sealed impermeable pouch containing said absorbent means; and means for opening said pouch for exposing said absorbent means for application of chemical reagents thereto.

5. A biological material sampling device for receiving and transporting material samples, said device comprising: a sheet of pliant impermeable material; absorbent means secured to said sheet for receiving a biological material smear; securement means on said sheet surrounding said absorbent means; impermeable closure means adapted to overlie said absorbent means and engage said securement means to form a sealed impermeable pouch containing said absorbent means; and means for opening said pouch for exposing said absorbent means.

6. The device of claim 5, wherein said means for opening said pouch is resealable.

7. A stool sampling device for obtaining direct anal stool samples, said device comprising:
(a) a first sheet of pliant impermeable material;
(b) a pad secured to one side of said first sheet, said pad being operable to receive a stool smear when said device is drawn across a patient's anus after defecation;

(c) a second sheet of pliant material disposed on said first sheet, said second sheet overlying said one side of said first sheet, and said second sheet including an opening therethrough aligned with said pad;

(d) first releasable adhesive means securing said second sheet to said first sheet whereby said second sheet can be peeled off of said first sheet after a stool smear has been deposited on said pad;

(e) means for hermetically sealing said pad within said first sheet after a stool smear has been deposited on said pad;

(f) means forming an opening in said first sheet which opening is aligned with said pad when the latter is sealed within said first sheet;

(g) a pliant impermeable cover sheet hermetically sealing said opening in said first sheet; and (h) second releasable adhesive means securing said cover sheet to the other side of said first sheet, said second adhesive means forming means whereby said cover sheet can be peeled away from said first sheet to uncover said opening in said first sheet to expose said pad for the application of detecting reagents to the stool smear, and whereby said cover sheet can be resealed to said first sheet after the stool smear has been tested.

8. The stool sampling device of claim 1, wherein said means for hermetically sealing comprises a portion of said first releasable adhesive means.

9. The stool sampling device of claim 1, wherein a portion of said second sheet is flocked with a layer of absorbent fibrous material in the area thereof surrounding said opening in said second sheet.

10. A stool sampling device for obtaining direct anal stool samples, said device comprising:

(a) a first elongated sheet of pliant impermeable material having opposed lateral half portions;

(b) a pad secured to one side of said first sheet, said pad being situated on one of said half portions of said first sheet, said pad being operable to receive a stool smear when said device is drawn across a patient's anus after defecation;

(c) a second sheet of pliant material overlying substantially all of said one side of said first sheet, said second sheet including an opening therethrough aligned with said pad, the obverse surface of at least the portion of said second sheet which overlies said one of said half portions of said first sheet being flocked with a layer of absorbent fibrous material;

(d) first releasable adhesive means securing said second sheet to said first sheet whereby said second sheet can be peeled off of said first sheet after a stool smear has been deposited on said pad, at least a portion of said first adhesive means providing means for hermetically sealing said pad within said first sheet when the other of said half portions of said first sheet is folded over said one of said half portions of said first sheet after removal of said second sheet.

(e) means forming an opening in said first sheet through said other half portion of said first sheet, said opening being aligned with said pad when said pad is hermetically sealed within said first sheet;

(f) a pliant impermeable cover sheet hermetically sealing said opening in said first sheet; and (g) second releasable adhesive means securing said cover sheet to the other side of said first sheet, said second adhesive means forming means whereby said cover can be peeled away from said first sheet to uncover said opening in said first sheet to expose said pad for the application of detecting reagents to the stool smear, and whereby said cover sheet can be resealed to said first sheet after the stool smear has been tested.

* * * * *